(12) United States Patent
Jung et al.

(10) Patent No.: US 8,746,056 B2
(45) Date of Patent: Jun. 10, 2014

(54) DISDROMETER SYSTEM HAVING A THREE-DIMENSIONAL LASER ARRAY UNIT

(75) Inventors: Jae-Won Jung, Seoul (KR); Ki-Ho Chang, Seoul (KR); Jin-Young Bae, Gyeonggi-do (KR); Chulkyu Lee, Seoul (KR); Gyuwon Lee, Daegu (KR); Young Jean Choi, Seoul (KR)

(73) Assignee: Korea Meterological Administration, Seoul (KR)

( * ) Notice: Subject to any disclaimer, the term of this patent is extended or adjusted under 35 U.S.C. 154(b) by 67 days.

(21) Appl. No.: 13/703,090

(22) PCT Filed: Aug. 23, 2010

(86) PCT No.: PCT/KR2010/005578
§ 371 (c)(1),
(2), (4) Date: Feb. 7, 2013

(87) PCT Pub. No.: WO2011/155664
PCT Pub. Date: Dec. 15, 2011

(65) Prior Publication Data
US 2013/0205890 A1    Aug. 15, 2013

(30) Foreign Application Priority Data
Jun. 10, 2010  (KR) ........................ 10-2010-0054814

(51) Int. Cl.
*G01W 1/00*    (2006.01)
(52) U.S. Cl.
USPC ..................................... 73/170.17; 73/170.18
(58) Field of Classification Search
None
See application file for complete search history.

(56) References Cited

U.S. PATENT DOCUMENTS

| | | | |
|---|---|---|---|
| 4,754,149 A * | 6/1988 | Wang | 250/573 |
| 7,660,517 B2 * | 2/2010 | Garg et al. | 396/77 |
| 7,688,249 B2 * | 3/2010 | Fischer et al. | 342/26 R |
| 2007/0132599 A1 | 6/2007 | DuFaux et al. | |
| 2013/0222179 A1 * | 8/2013 | Jeong | 342/352 |

FOREIGN PATENT DOCUMENTS

| | | |
|---|---|---|
| JP | 08027713 A | 1/1996 |
| JP | 2008157765 A | 7/2008 |
| KR | 1019990068430 A | 9/1999 |

OTHER PUBLICATIONS

International Search Report; International Application No. PCT/KR2010/005578; Jul. 27, 2011; Korean Intellectual Property Office.

* cited by examiner

*Primary Examiner* — Andre Allen
(74) *Attorney, Agent, or Firm* — Stevens & Showalter LLP

(57) ABSTRACT

Provided is a disdrometer system having a three-dimensional laser array unit, including: a plurality of laser transmitting parts which are arranged on an inner side of a cylindrical body to generate a laser beam; a plurality of laser receiving parts which are arranged on the inner side of the cylindrical body to correspond to the laser transmitting parts; and a laser control part which converts a cut-off signal of the laser beam, which is cut-off by precipitation drops flowing into the inner side of the cylindrical body, into an electrical signal, and records the converted electrical signal. Thus, the disdrometer system has an effect that the shape, volume, number, falling velocity of precipitation drops, and the intensity, density and weight of rainfall can be integrally measured.

9 Claims, 2 Drawing Sheets

US 8,746,056 B2

DISDROMETER SYSTEM HAVING A THREE-DIMENSIONAL LASER ARRAY UNIT

TECHNICAL FIELD

The present invention relates to a disdrometer system having a three-dimensional laser array unit, more specifically, to a disdrometer system which is configured such that a laser transmitting part, a laser receiving part and a weight measuring part are three-dimensionally arranged so that the shape, volume, number, and falling velocity of precipitation drops, and the intensity, weight and density of rainfall can be integrally measured.

BACKGROUND ART

Observation apparatuses for observing precipitation phenomena among meteorological phenomena have been developed for more accurate observation in the world since Korean rain gauge was invented in 1441 by King Sejong.

Among these apparatuses, a rain gauge, which is a representative apparatus for observing the rain, is divided into various kinds such as a water storage type cylindrical rain gauge, a water storage type self-recording rain gauge, an inverted type rain gauge, a weight type rain gauge, a load cell type rain gauge and the like. Generally, in the case of snow, there is an observation apparatus for the measurement of snow cover. According to observation methods, the observation apparatus is divided into the kinds such as a snow measuring plate using direct measurement with the eye of a person, an infrared-ray snow observation apparatus using an infrared ray method, a video snow observation apparatus using a video camera, an ultrasonic snow observation apparatus using ultrasonic waves, a laser snow observation apparatus using a laser, and the like.

The observation of precipitation phenomena was focused to typically observe the amount or depth of precipitation. However, since a remote sensing apparatus such as radar, a meteorological satellite and the like was developed, the need to accurately observe the size, shape, concentration, falling velocity of precipitation drops, and the intensity and weight of rainfall has arisen for the quantitative forecast of precipitation.

As a representative apparatus devised for observing precipitation drops in the world, a disdrometer using an optical method has been currently developed and used. This disdrometer is an apparatus for measuring the size and falling velocity of precipitation drops, the intensity and visibility of rainfall, the shape of precipitation and the like, and generates the horizontal beam of rays from a laser transmitter and converts it into an electrical signal in a receiver. In spite of this, it is problematic that the disdrometer adopts a two-dimensional laser method, and thus the shape, volume, and density of precipitation drops (i.e. rain, snow), and the water equivalent of precipitation drops are not accurately observed.

DETAILED DESCRIPTION OF THE INVENTION

Technical Problem

The present invention has been made keeping in mind the above problems occurring in the related art. An aspect of the present invention provides a disdrometer system which makes up for the disadvantages of apparatuses for observing precipitation phenomena among meteorological phenomena such as a rain gauge for observing the rain, a snow-depth gauge for observing the snow and a disdrometer for observing the precipitation drops, and which is capable of observing the three-dimensional shape, size, concentration, and falling velocity of precipitation drops, the intensity of rainfall, and the immediate water equivalent of precipitation in several microsecond ($\mu s$) and several microgram ($\mu g$).

Technical Solution

According to an aspect of the present invention, there is provided a disdrometer system having a three-dimensional laser array unit, including: a plurality of laser transmitting parts which are arranged on an inner side of a cylindrical body and generates a laser beam; a plurality of laser receiving parts which are arranged on the inner side of the cylindrical body to correspond to the laser transmitting s; and a laser control part which converts a cut-off signal of the laser beam, which is cut-off by precipitation drops flowing into the inner side of the cylindrical body, into an electrical signal, and records the converted electrical signal.

Also, the laser transmitting parts and the laser receiving parts may be alternately disposed on the inner side of the cylindrical body.

Also, the laser transmitting parts may have three-dimensional coordinate values, respectively.

Also, the laser control may record the three-dimensional coordinate values of the laser transmitting parts in which the cut-off signal is detected, and the electrical signal in a time unit of more than 1 $\mu s$.

Also, the precipitation drops passing through the cylindrical body may flow into a water storage bottle having a high-precision electronic scale.

Also, the electronic scale may measure a weight ranging from 1 $\mu g$ to 300 kg in the time unit of more than 1 $\mu s$.

Also, the disdrometer may further include a weight measurement controlling part for calculating and transmitting the weight measured by the electronic scale and a value converted into a unit of the amount of precipitation (mm).

Also, the water storage bottle may automatically discharge the flowing precipitation when the amount of precipitation which flows in the water storage bottle exceeds 1,100 mm or 300 kg.

Also, the water storage bottle may further include an outlet for automatically discharging the flowing precipitation within one minute when the amount of precipitation, which flows in the water storage bottle, exceeds 1,100 mm or 300 kg, or when the state of non-precipitation is maintained for ten minutes.

Also, the disdrometer system may further include a precipitation detecting sensor.

Advantageous Effects

According to the present invention, the disdrometer system having the three-dimensional laser array unit is advantageous that the shape, size, concentration and falling velocity of precipitation drops, and the intensity and weight of rainfall can be integrally measured.

BEST MODE FOR CARRYING OUT THE INVENTION

Hereinafter, preferred embodiments of a disdrometer having a three-dimensional laser array unit according to the present invention will be described in detail with reference to the accompanying drawings.

Figure 1:
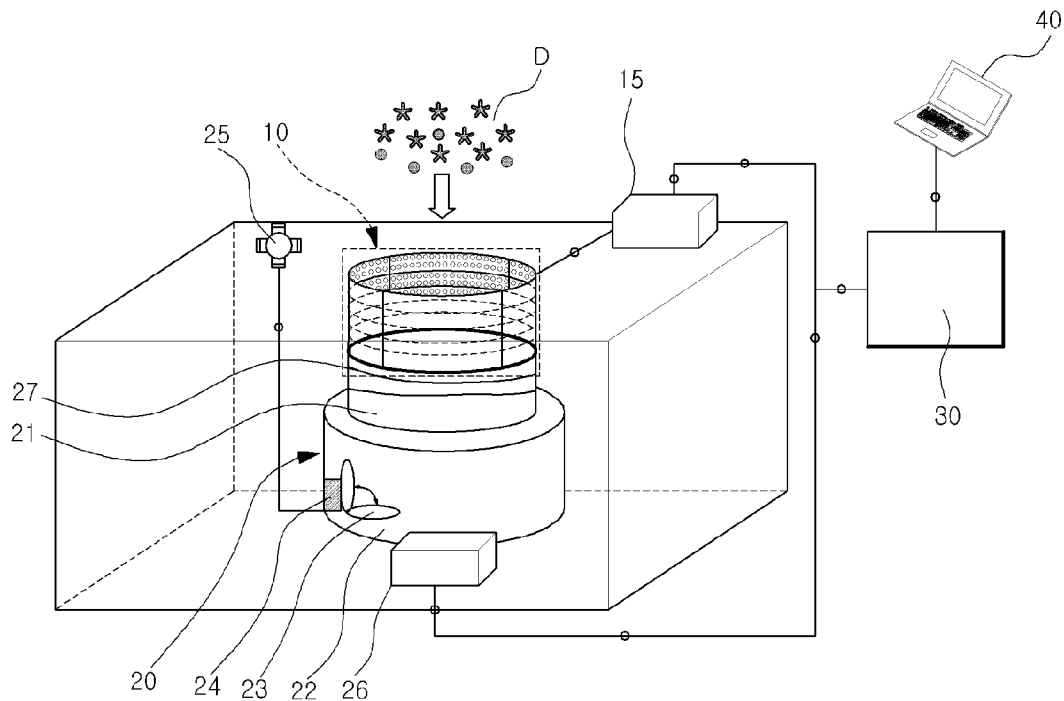
FIG. 1 is a configuration view of a disdrometer system having a three-dimensional laser array unit according to the present invention.
Figure 2:
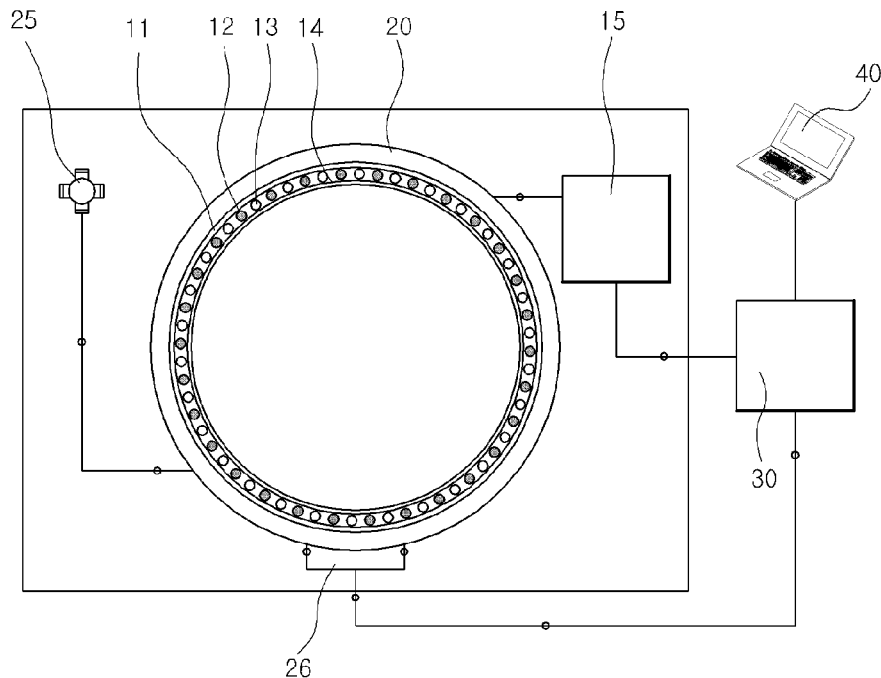
FIG. 2 is a plane view of the three-dimensional laser array unit of FIG. 1.
Figure 3:
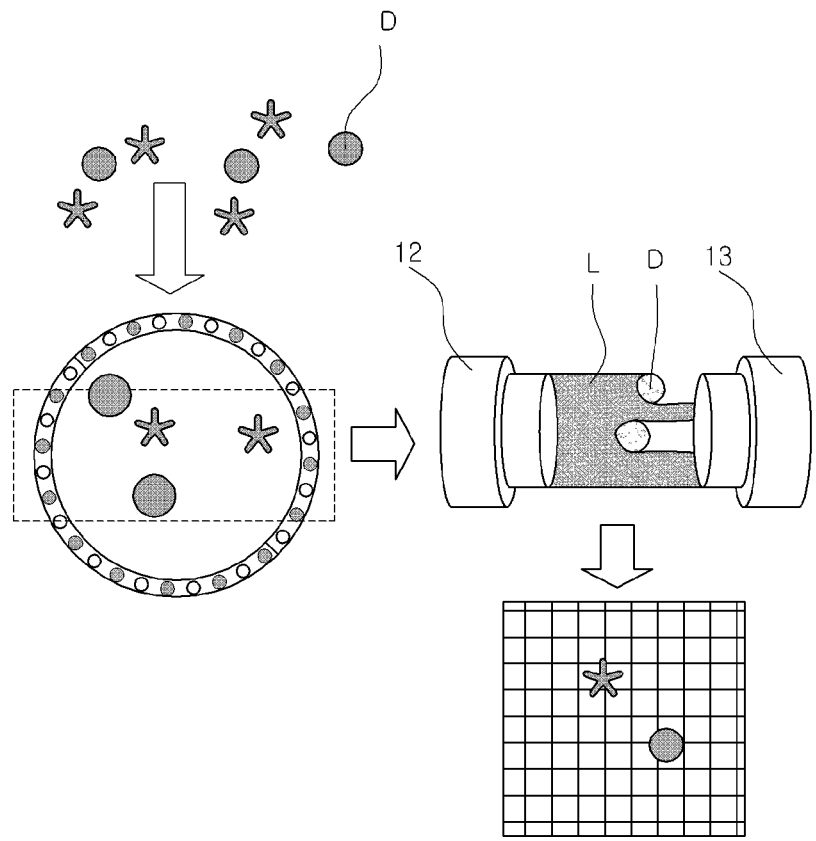
FIG. 3 and FIG. 4 are schematic diagrams showing the shape, volume, number and the like of precipitation drops measured using a laser.
Figure 4:
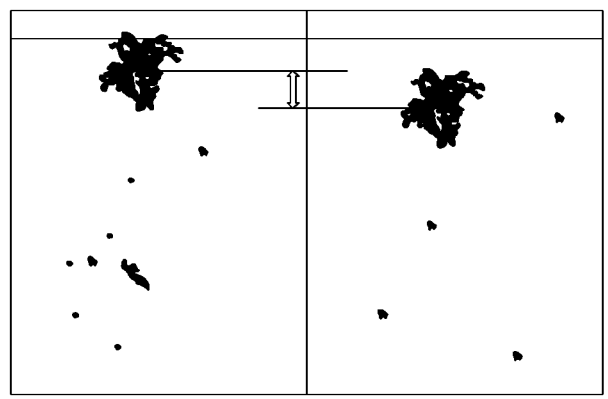

FIG. 1 is a configuration view of a disdrometer system having a three-dimensional laser array unit according to the present invention. FIG. 2 is a plane view of the three-dimensional laser array unit of FIG. 1. FIG. 3 and FIG. 4 are schematic diagrams showing the shape, volume, number and the like of precipitation drops measured using a laser.

Referring to FIG. 1 and FIG. 2, a disdrometer system according to the present invention includes a three-dimensional laser array unit 10 and a water storage bottle unit 20. The three-dimensional laser array unit 10 includes a cylindrical body 11 and a laser transmitting part 12 and a laser receiving part 13 which are installed at an inner wall of the cylindrical body 11. A cover (not drawn) for opening and closing the three-dimensional laser array unit 10 may be installed at an upper portion of the cylindrical body. The laser transmitting part 12 and the laser receiving part 13 are alternately installed on an inner side of the cylindrical body 11 to be exact. One laser transmitting part 12 and one laser receiving part 13 corresponding thereto are installed at the inner wall of sides opposite each other, provided that a center point of the cylindrical body is a symmetrical point. The laser transmitting part 12 and the laser receiving part 13 have three-dimensional coordinate values (x, y, z), respectively, according to an installation location.

A protective wall 14 is installed at an inner side of the laser transmitting part 12 and the laser receiving part 13. The protective wall 14 prevents the laser transmitting part 12 and the laser receiving part 13 from being damaged due to the precipitation drops D.

Referring to FIG. 3 and FIG. 4, when the precipitation drops (i.e. rain, snow) enters through an inlet of the apparatus, the laser transmitting part 12 generates a laser beam L, and the laser receiving part 13 receives the laser beam L and converts it into an electrical signal. The laser beam generated from the laser transmitting part 12 is incident to a photoelectric device (not drawn) of the receiving part. When there are no precipitation drops, the laser receiving part outputs a maximum voltage value. When there are the precipitation drops D passing through the laser beam, the precipitation drops block off a part of the laser beam as much as a diameter thereof, and the laser receiving part 13 outputs the reduced voltage value. The reduced output value of the electrical signal is input as the previously inputted unique three-dimensional coordinate values (x, y, z) and is stored into a data logger 30. At this time, the signal value is observed and recorded in a time unit of several microsecond (µs). A display system 40 measures the shape, volume and number of precipitation drops based on the observed data, and calculates and outputs a falling velocity based on a measurement difference between an upper laser beam and a lower laser beam. Furthermore, the display system calculates and outputs a density based on the measured volume and mass.

The laser generation and reception, and conversion into the electrical signal, which are performed by the laser transmitting and receiving parts, are performed through the laser control part 15. The laser control part 15 is connected to the data logger 30.

The precipitation passing through the laser transmitting part 12 and the laser receiving part 13 flows and is stored into a weight measuring part 20. The weight measuring part 20 includes a water storage bottle 21 and an electronic scale 22. In the water storage bottle 21, an outlet 23 operated by an electric discharge controlling sensor 24 is installed, and the electric discharge controlling sensor 24 is connected to a precipitation detecting sensor 25. As the precipitation detecting sensor 25, a publicly known precipitation detecting sensor such as a piezoelectric element method or a photo sensor method may be used. When the precipitation detecting sensor 25 detects the precipitation, a signal is sent to the electric discharge controlling sensor. Thus, the outlet 23 of the water storage bottle 21 is opened so that the precipitation remaining in the water storage bottle may be discharged.

The electronic scale 22 measures a weight of rainwater preserved in the water storage bottle 21 in a time unit of several microsecond (µs), measuring the weight up to 300 kg at a unit of several microgram (µg). The measured weight of the amount of precipitation is transmitted to the data logger 30 in real time. The data such as the unit of weight, and values in which the weight is converted into a unit (mm) of the amount of precipitation is stored.

In a case where the amount of precipitation which is sequentially measured shows more than 1,100 mm in the water storage bottle 21 or exceeds 300 kg in the electronic scale, or in a case where the state of non-precipitation is maintained for ten minutes, the precipitation is automatically discharged through the outlet 23 within one minute by the operation of the electric discharge controlling sensor 24, and a discharging time is recorded into a system controlling part 31. Furthermore, if the state of non-precipitation is maintained for ten minutes after the generation of precipitation, the precipitation preserved in the water storage bottle 21 is automatically discharged within one minute.

The water storage bottle 21 includes a heat wire 27. The heat wire 27 functions to reduce a measurement error by evaporating the precipitation remaining in the water storage bottle 21 prior to the starting of measurement. When the precipitation detecting sensor 25 detects the precipitation, a water storage bottle controlling part 26 evaporates and removes the precipitation drops remaining in the water storage bottle 21 by setting the heat wire 27 in operation. The weight measurement of the electronic scale 22, and the operation of the electric discharge controlling sensor and the heat wire 27 are performed through the weight measurement controlling part 26.

The laser control part 15 and the weight measurement controlling part 26 are connected to the data logger 30 and the system controlling part 31, respectively. The display system 40 commands the starting of measurement by a precipitation signal detected from the precipitation detecting sensor 25, and calculates and displays the three-dimensional shape, volume, number, falling velocity, and weight of precipitation drops based on observation records stored in the data logger 30.

As previously described, in the detailed description of the invention, having described the detailed exemplary embodiments of the invention, it should be apparent that modifications and variations can be made by persons skilled without deviating from the spirit or scope of the invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims and their equivalents.

INDUSTRIAL APPLICABILITY

The disdrometer system having the three-dimensional array unit according to the present invention can be used in the industry field of observation apparatuses for observing precipitation phenomena among meteorological phenomena.

What is claimed is:

1. A disdrometer having a three-dimensional laser array unit, comprising:
   a plurality of laser transmitting parts which are arranged on an inner side of a cylindrical body to generate a laser beam;
   a plurality of laser receiving parts which are arranged on the inner side of the cylindrical body to correspond to the laser transmitting parts; and
   a laser control part which converts a cut-off signal of the laser beam, which is cut-off by precipitation drops entered into the inner side of the cylindrical body, into an electrical signal, and records the converted electrical signal.

2. The disdrometer of claim 1, wherein the laser transmitting parts and the laser receiving parts are alternately disposed on the inner side of the cylindrical body.

3. The disdrometer of claim 2, wherein the laser transmitting parts and the laser receiving parts have three-dimensional coordinate values, respectively.

4. The disdrometer of claim 1, wherein the laser control part records the three-dimensional coordinate values of the laser transmitting parts in which the cut-off signal is detected and the electrical signal in a time unit of more than 1 µs.

5. The disdrometer of claim 1, wherein the precipitation drops passing through the cylindrical body flow into a water storage bottle having a high-precision electronic scale.

6. The disdrometer of claim 5, wherein the electronic scale measures a weight ranging from 1 µg to 300 kg, measuring the weight in a time unit of more than 1 µs.

7. The disdrometer of claim 6, further comprising a weight measurement controlling part which calculates and transmits the weight measured by the electronic scale and a value converted into a unit of the amount of precipitation.

8. The disdrometer of claim 5, wherein the precipitation, which flows into the water storage bottle, is automatically discharged within one minute when the state of non-precipitation is maintained for ten minutes.

9. The disdrometer of claim 1, further comprising a precipitation detecting sensor.

* * * * *